(12) United States Patent
Iwaki et al.

(10) Patent No.: US 7,169,583 B2
(45) Date of Patent: Jan. 30, 2007

(54) METHOD FOR THE DETECTION OF GENE WITH DNA MICRO-ARRAY

(75) Inventors: Yoshihide Iwaki, Asaka (JP); Hiroshi Shinoki, Asaka (JP); Osamu Seshimoto, Asaka (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 419 days.

(21) Appl. No.: 10/160,241

(22) Filed: Jun. 4, 2002

(65) Prior Publication Data

US 2004/0086853 A1    May 6, 2004

(30) Foreign Application Priority Data

Jun. 5, 2001    (JP) .............................. 2001-169317

(51) Int. Cl.
*C12P 19/34*    (2006.01)
*C12Q 1/68*    (2006.01)
*C07H 21/00*    (2006.01)

(52) U.S. Cl. .................. 435/91.1; 435/6; 435/91.2; 536/24.3

(58) Field of Classification Search .................. 435/6, 435/91.1, 91.2; 536/24.3
See application file for complete search history.

(56) References Cited

U.S. PATENT DOCUMENTS 6,485,903 B1 * 11/2002 Mayrand ........................ 435/6

FOREIGN PATENT DOCUMENTS

EP    0347137    * 12/1989
JP    2001-228152    8/2001
WO    WO00/61282 A1    * 10/2000

OTHER PUBLICATIONS

Zhen Guo et al.; Nucleic Acids Research, vol. 22, No. 24, pp. 5456-5465, 1994.
Fusao Kimizuka et al.; Protein, Nucleic Acid, Enzyme, vol. 43, No. 13 (1998), pp. 2004-2011.
Tomi Pastinen et al.; Genome Research; vol. 7, 1997, pp. 606-614.

* cited by examiner

*Primary Examiner*—Jezia Riley
(74) *Attorney, Agent, or Firm*—Birch, Stewart, Kolasch & Birch, LLP

(57) ABSTRACT

An object of the present invention is to provide a means for simply performing a gene analysis without performing complicated operations. The present invention provides a method for the detection of a nucleic acid, comprising the steps of: performing a PCR reaction or a reverse transcription reaction by adding a template nucleic acid to a solid support on which a nucleic acid is fixed; and hybridizing the nucleic acid fixed on said solid support with the nucleic acid synthesized by the PCR reaction or the reverse transcription reaction.

15 Claims, 1 Drawing Sheet

METHOD FOR THE DETECTION OF GENE WITH DNA MICRO-ARRAY

TECHNICAL FIELD

The present invention relates to a method for the detection of a nucleic acid by using a DNA chip that is very useful for simultaneous analysis of expression, mutation, polymorphism or the like of a gene. More specifically, the present invention provides a method for promptly detecting a gene in a DNA chip of a covalent bonding type.

BACKGROUND OF THE INVENTION

As a powerful means for analyzing expression, mutation, polymorphism or the like of a gene, DNA chips (or DNA micro-arrays) have been proposed, and some DNA chips are put into practical use. As for a method for the preparation of DNA chips, such methods are known that surface of a solid support is previously processed to make the surface obtain plus charge, then the DNA is directly fixed to the solid support electrostatically; that synthesized oligonucleotides are fixed to the surface of the solid support via a covalent bond; or that DNA is directly synthesized on the surface of the solid support. However, these methods have merits and demerits, and an appropriate one is utilized depending on its purpose of use.

In the case where a DNA fragment to be fixed is cDNA (complementary DNA synthesized by utilizing mRNA as a template) or PCR products (DNA fragment that is amplified from the cDNA by a PCR method), in general, cDNAs or PCR products are dotted to the surface of the solid support of which the surface is treated with a polycationic compound (poly-lysine, polyethyleneimine or the like) by using a spotting device provided in a DNA chip preparation device, and are electrostatically bound to the solid support by utilizing the charge of DNA.

However, in these micro-arrays of an electrostatically bound type, an oligonucleotide of a short chain is released from the solid support at higher temperatures since the bonding force to the support is increased in proportion to length of a DNA to be fixed.

Therefore, in the case where a DNA fragment to be fixed is a synthesized oligonucleotide, an oligonucleotide into which a reactive group has been introduced is synthesized, then the oligonucleotide is dotted to the surface of the surface-treated solid support and is bound thereto via covalent bond ("Protein, Nucleic Acid, Enzyme" Vol. 43 (1998) 2004–2011; Lamture, J. B et al., Nucl. Acids Res., 22, 2121–2125, 1994; Guo, Z. et al., Nucl. Acids Res., 22, 5456–5465, 1994). For example, a method is known in which an amino group-introduced oligonucleotide is reacted with the slide glass to which an amino group has been introduced, in the presence of PDC (p-phenylene diisothiocyanate), and another method is known in which an aldehyde group-introduced oligonucleotide is reacted with said slide glass. By using these two methods, an oligonucleotide is stably fixed to the surface of the solid support, as compared with the above-described method which utilizes charge of the DNA.

The slide glass to which an oligonucleotide is fixed is often used to detect mutation or polymorphism of the gene. An analyte used for analysis of mutation or polymorphism is often selected by amplifying a region containing a polymorphism portion by PCR reaction from a genome DNA which is a sample. However, the operation in this method was complicated since it requires two steps of reaction; that is, the PCR reaction and a subsequent hybridization reaction.

SUMMARY OF THE INVENTION

An object of the present invention is to provide a means for simply performing a gene analysis without performing complicated operations.

In order to achieve the above object, the inventors have studied earnestly. As a result, they have found that a gene can be simply detected with high sensitivity by simultaneously performing the PCR reaction and the hybridization reaction on a slide glass, although conventionally these reactions were separately performed in the gene analysis.

Thus, according to the present invention, there is provided a method for the detection of a nucleic acid, comprising the steps of:

performing a PCR reaction or a reverse transcription reaction by adding a template nucleic acid to a solid support on which a nucleic acid is fixed; and hybridizing the nucleic acid fixed on said solid support with the nucleic acid synthesized by the PCR reaction or the reverse transcription reaction.

Preferably, the nucleic acid is fixed on the surface of the solid support to which a group of vinylsulfonyl group or its reactive precursor has been fixed respectively by covalent bond via a linking group.

Preferably, a linked body of the vinylsulfonyl group or its reactive precursor and the linking group is shown by the following formula:

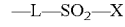

in the formula, X represents —CR$^1$=CR$^2$(R$^3$) or —CH(R$^1$)—CR$^2$(R$^3$)(Y); each of R$^1$, R$^2$ and R$^3$ represents independently from each other an atom or a group selected from the group consisted of a hydrogen atom, an alkyl group having 1 to 6 carbon atoms, an aryl group having 6 to 20 carbon atoms and an aralkyl group having 7 to 26 carbon atoms in total containing an alkyl chain having 1 to 6 carbon atoms; Y represents an atom or a group selected from the group consisted of a halogen atom, —OSO$_2$R$^{11}$, —OCOR$^{12}$, —OSO$_3$M and a quaternary pyridinium group; R$^{11}$ represents a group selected from the group consisted of an alkyl group having 1 to 6 carbon atoms, an aryl group having 6 to 20 carbon atoms and an aralkyl group having 7 to 26 carbon atoms in total containing an alkyl chain having 1 to 6 carbon atoms; R$^{12}$ represents a group selected from the group consisted of an alkyl group having 1 to 6 carbon atoms and a halogenated alkyl group having 1 to 6 carbon atoms; M represents an atom or a group selected from the group consisted of a hydrogen atom, an alkali metal atom and an ammonium group; and L represents a liking group.]

Preferably, X is a vinyl group represented by —CH=CH$_2$.

Preferably, L is a linking group containing an atom of bivalent or more other than a carbon atom.

Preferably, L is a linking group having a linking portion selected from the group consisted of —NH—, —S— and —O—.

Preferably, L is a linking group represented by —(L$^1$)$_n$—NH—(CR$^1$R$^2$)$_2$— or —(L$^1$)$_n$—S—(CR$^1$R$^2$)$_2$— wherein R$^1$ and R$^2$ represent the same meaning as defined above; L$^1$ represents a linking group; and n is 0 or 1.

Preferably, L is a linking group represented by —(L$^1$)$_n$—NHCH$_2$CH$_2$— wherein L$^1$ represents a linking group; and n is 0 or 1.

Preferably, $L^1$ is a linking group containing a group represented by —OSi— and n is 1.

Preferably, the solid support is a sheet-like substrate selected from the group consisted of a glass substrate, a resin substrate, a glass substrate or a resin substrate the surface of which is treated with a silane coupling agent, and a glass substrate or a resin substrate having a covering layer on its surface.

Preferably, the solid support is a sheet-like substrate selected from the group consisted of a silicate glass substrate, a silicate glass substrate the surface of which is treated with a silane coupling agent, and a silicate glass substrate the surface of which is covered with an organic covering layer.

Preferably, the nucleic acid fixed on the solid support is a nucleotide derivative or its analog.

Preferably, the nucleotide derivative or its analog is an oligonucleotide, a polynucleotide or a peptide nucleic acid.

Preferably, a nucleotide to which a detectable label is introduced is synthesized in the PCR reaction or the reverse transcription reaction.

DETAILED DESCRIPTION OF THE INVENTION

Figure 1:
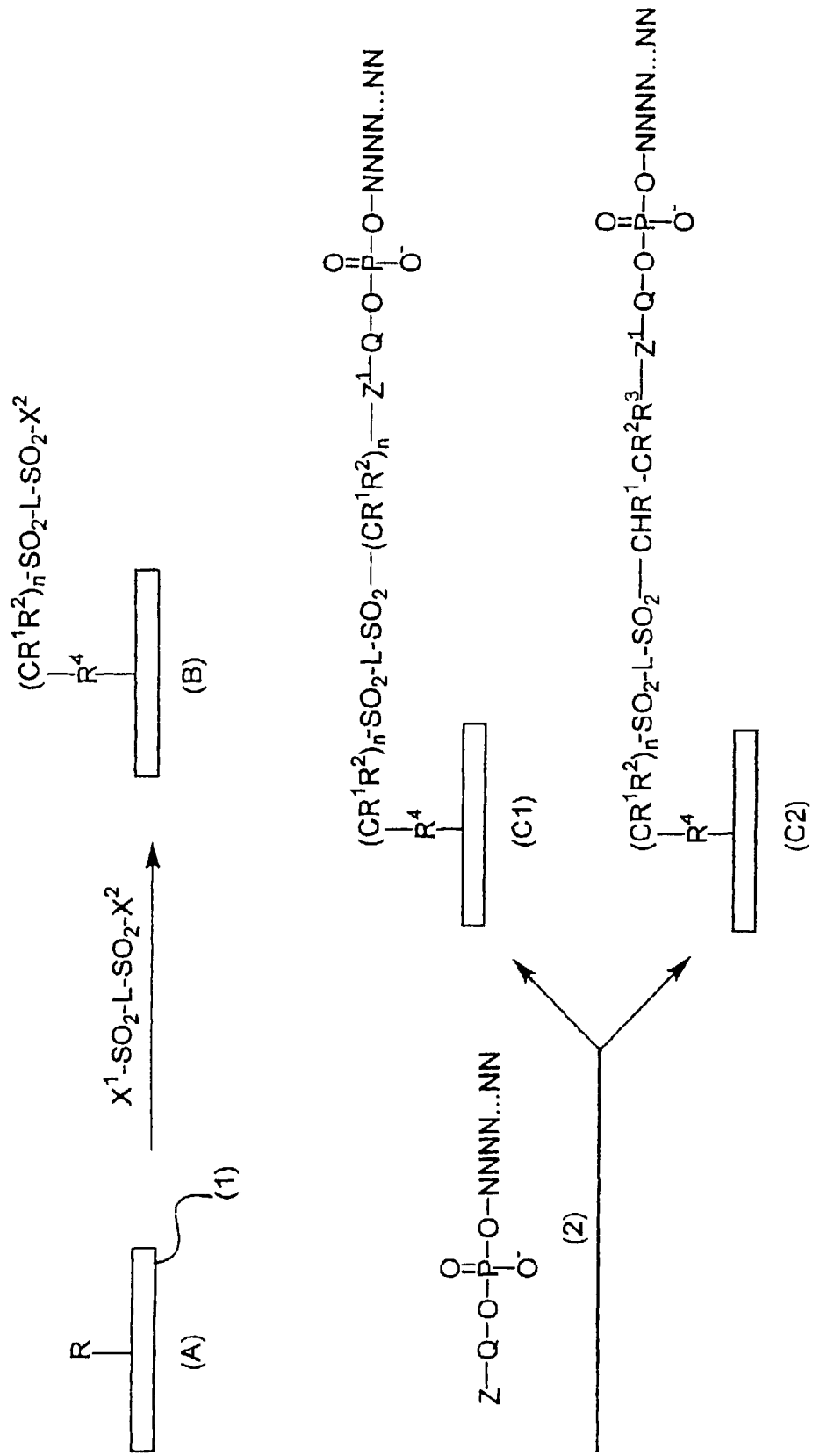
FIG. 1 is a schematic figure showing a typical oligonucleotide fixed-solid support and a typical method of fixing an oligonucleotide, which can be used in the present invention.

Embodiments of the present invention are described in detail below.

The method for the detection of a nucleic acid according to the present invention is characterized in that it comprises the steps of:

performing a PCR reaction or a reverse transcription reaction by adding a template nucleic acid to a solid support on which a nucleic acid is fixed; and hybridizing the nucleic acid fixed on the solid support with the nucleic acid synthesized by the PCR reaction or the reverse transcription reaction.

A feature of the present invention resides in that two reactions of a synthesizing reaction of a nucleic acid by a PCR reaction or a reverse transcription reaction using a template nucleic acid and a hybridization reaction of the nucleic acid generated by said synthesizing reaction of the nucleic acid with a nucleic acid previously fixed on the solid support, are carried out continuously. In conventional methods, operations were complicated since a PCR reaction for amplifying a target gene from a template nucleic acid such as sample genome DNA and hybridization were performed separately. In the present invention, on the contrary, a synthesizing reaction of a target gene to be detected and hybridization are performed in one operation on the solid support, thereby enabling a simple analysis of a gene without performing complicated operations.

The solid support used in the present invention to fix a nucleic acid is preferably those of a constitution where a group of vinylsulfonyl group or its reactive precursor has been bound and fixed to the surface of the solid support via a linking group by covalent bond, respectively. The solid support having a fixed nucleic acid which is used in the present invention, can be obtained by binding a nucleic acid to a reactive solid support via covalent bond.

The reactive solid support before the fixation of the nucleic acid can be manufactured, for example, by preparing a solid support to the surface of which a reactive group has been previously introduced, and then bringing this solid support into contact with a compound having a reactive group capable of forming a covalent bond by reacting with a reactive group provided to the surface of the support at one of end portions or nearby the end portion and having a vinyl sulfonyl group or a reactive precursor group of the vinyl sulfonyl group at the other end portion or nearby the end portion.

It is preferable that the solid support is a particularly hydrophobic or lower hydrophilic substrate having a flat and smooth surface. Moreover, a substrate having a surface of lower degree of flatness with convex and concave portions can be also employed. As a substance for the solid support, a variety of porous substances such as glass, cement, ceramics or new ceramics such as potteries or the like, polymers such as polyethylene terephthalate, cellulose acetate, polycarbonate of bisphenol A, polystyrene, polymethyl methacrylate or the like, silicon, activated carbon, porous glass, porous ceramics, porous silicon, porous activated carbon, woven fabric, knitted fabric, non-woven fabric, filter paper, short fiber, membrane filter or the like can be listed. It is preferable that the size of a fine hole of a porous substance is in the range from 2 to 1000 nm, and particularly preferable in the range from 2 to 500 nm. It is particularly preferable that the substance of a solid support is a glass or silicon. This is because of the easiness of surface treatment and the easiness of analysis by an electrochemical method. It is preferable that the thickness of the solid support is in the range from 100 to 2000 µm.

As for the solid support used for manufacturing a reactive solid support, a variety of solid supports conventionally used for manufacturing DNA chips or proposed for manufacturing the DNA chip can be preferably utilized. As an example of such a solid support, a glass substrate, a resin substrate, a glass substrate or resin substrate surface treated by a silane coupling agent, or a glass substrate or a resin substrate having a covering layer on the surface, or the like can be listed. As for the solid support, a silicate glass substrate, a silicate glass substrate surface treated by a silane coupling agent, or a silicate glass substrate covered by an organic covering layer is particularly preferable. Moreover, it may be an electrode substrate used as a substrate of a DNA chip used for an electrochemical analyzing method. Moreover, it may be a variety of functional substrates such as a substrate used for the above-described surface plasmon resonance (SPR) biosensor, a charge coupled device (CCD) or the like. Furthermore, adding to these substances, a solid support in a particle shape can be also employed.

It is desirable to perform the covering treatment on the surface of the solid support by a polymer containing an amino group such as a polycationic compound (for example, poly-L-lysine, polyethyleneimine, polyalkylamine or the like is preferable, and poly-L-lysine is more preferable) on side chain in order to bind and fix bifunctional reactive compounds such as divinyl sulfone compound by covalent bond (in this case, the reactive group introduced to the surface of the solid support is an amino group). Alternatively, the surface of the solid support may be brought into contact and treated with a surface treatment agent having a reactive group such as a silane coupling agent which reacts with the surface of the solid support and a reactive group such as an amino group.

In the case where the covering treatment is performed with a polycationic compound, an amino group or a mercapto group is introduced to the surface of the solid support by electrostatically binding between the polymer compound and the surface of the solid support. On the other hand, in the case where the surface treatment is performed by a silane coupling agent, the amino group or mercapto group stably exists on the surface of the solid support since it is bound and fixed to the surface of the solid support by covalent bond. In addition to an amino group or a mercapto group, an aldehyde group, an epoxy group, a carboxyl group or a hydroxyl group may be also preferably introduced.

As a silane coupling agent having an amino group, it is preferable to use γ-aminopropyltriethoxy silane, N-β(aminoethyl)-γ-aminopropyltrimethoxy silane, or N-β(aminoethyl)-γ-aminopropylmethyldimethoxy silane, and particularly it is preferable to use γ-aminopropyl triethoxy silane.

The treatment with a silane coupling agent may be performed in combination with the treatment using a polycationic compound. Using this method, an electrostatical interaction between a hydrophobic- or a low hydrophilic-solid support and DNA fragments can be promoted. A layer consisted of a hydrophilic polymer having a charge or a layer consisted of a crosslinking agent may be further provided on the surface of the solid support treated by a polycationic compound. As a result of providing such a layer, the height of the convex and concave portions of the solid support treated by the polycationic compound can be reduced. Depending on the types of the solid supports, it is possible that a hydrophilic polymer is contained in the support, and the solid support subjected to such a treatment can be also preferably used.

On the surface of the usually utilized solid support for a DNA chip, a large number of regions previously fractioned or expected are set and provided, and in each region, as described above, a reactive group which is capable of reacting with bifunctional reactive compound such as divinyl sulfone compound or the like has been previously introduced. A reactive group such as the above-described amino group, mercapto group or hydroxyl group or the like is provided on the surface of each region of the solid support which is to be employed. However, on a solid support not having such a reactive group, as described above, the introduction of a reactive group is performed by surface treatment using a silane coupling agent, or by utilizing a method of coating and covering a polymer or the like having a reactive group such as an amino group on side chain on the surface of the solid support.

In the solid support equipped with a reactive group, as a result of bringing it into contact with a bifunctional reactive compound such as divinyl sulfone compound or the like, the reactive group and bifunctional reactive compound are reacted to form a covalent bond, the reactive group portion of the solid support is extended, and a reactive chain having a vinyl sulfonyl group or its reactive precursor group at its end or nearby the end is formed, thereby providing a reactive solid support used in the present invention.

In a reactive solid support, a linked body of a vinyl sulfonyl group or its reactive precursor group and a linking group introduced on the surface of the reactive solid support is desirably a linked body represented by the following formula (1):

—L—SO$_2$—X     (1)

In the above-described formula (1), X represents —CR$^1$=CR$^2$R$^3$ or —CHR$^1$—CR$^2$R$^3$Y (reactive precursor group). Each of R$^1$, R$^2$ and R$^3$ represents independently from each other a hydrogen atom, an alkyl group having 1 to 6 carbon atoms, an aryl group having 6 to 20 carbon atoms, or an aralkyl group having 7 to 26 carbon atoms in total containing an alkyl chain having 1 to 6 carbon atoms.

Examples of an alkyl group having 1 to 6 carbon atoms include a methyl group, an ethyl group, an n-propyl group, an n-butyl group, and an n-hexyl group. A methyl group is particularly preferable. Aryl groups include a phenyl group and a naphthyl group. It is preferable that each of R$^1$, R$^2$ and R$^3$ represents a hydrogen atom, respectively.

Y represents a group which is substituted by a nucleophilic reagent such as —OH, —OR$^0$, —SH, NH$_3$, NH$_2$R$^0$ (wherein R$^0$ represents a group such as alkyl group except for hydrogen atom), or a group which is eliminated as "HY" by base. Examples thereof include a halogen atom, —OSO$_2$R$^{11}$, —OCOR$^{12}$, —OSO$_3$M, or a quaternary pyridinium group (R$^{11}$ represents an alkyl group having 1 to 6 carbon atoms, an aryl group having 6 to 20 carbon atoms, or an aralkyl group having 7 to 26 carbon atoms in total containing an alkyl chain having 1 to 6 carbon atoms; R$^{12}$ represents an alkyl group having 1 to 6 carbon atoms or halogenated alkyl group having 1 to 6 carbon atoms; M represents a hydrogen atom, an alkaline metal atom, or an ammonium group).

L represents a bivalent or more than bivalent linking group for linking the solid support or a linking group binding to the solid support with the above-described —SO$_2$—X group. However, L may be a single bond. Examples of the bivalent linking groups include an alkylene group having 1 to 6 carbon atoms, an aliphatic cyclic group having 3 to 16 carbon atoms, an arylene group having 6 to 20 carbon atoms, a heterocyclic group having 2 to 20 carbon atoms containing 1 to 3 hetero atoms selected from the group consisted of N, S and P, a group containing one group or the combination of a plurality of groups selected from the group consisted of —O—, —S—, —SO—, —SO$_2$—, —SO$_3$—, —NR$^{11}$—, —CO— and their combinations are preferable. R$^{11}$ is preferably a hydrogen atom, an alkyl group having 1 to 15 carbon atoms, an aryl group having 6 to 20 carbon atoms, or an aralkyl group having 7 to 21 carbon atoms containing an alkyl group having 1 to 6 carbon atoms, and more preferably a hydrogen atom or an alkyl group having 1 to 6 carbon atoms, and particularly preferably a hydrogen atom, amethyl group or an ethyl group.

In the case where L represents a group containing the combination of two or more of the groups selected from the group consisted of —NR$^{11}$—, —SONR$^{11}$—, —CONR$^{11}$—, —NR$^{11}$COO—, and —NR$^{11}$CONR$^{11}$—, these R$^{11}$ may bind each other to form a ring.

An alkyl group of R$^{11}$, an aryl group of R$^{11}$ and an aralkyl group of R$^{11}$ may have a substituent. Such substituents include an atom or a group selected from the group consisted of a hydroxyl group, an alkoxy group having 1 to 6 carbon atoms, an alkenyl group having 1 to 6 carbon atoms, a carbomoyl group having 2 to 7 carbon atoms, an alkyl group having 1 to 6 carbon atoms, an aralkyl group having 7 to 16 carbon atoms, an aryl group having 6 to 20 carbon atoms, an sulfamoyl group (or its Na salt, K salt or the like), a sulfo group (or its Na salt, K salt or the like), a carboxylic acid group (or its sodium salt, potassium salt or the like), a halogen atom, an alkenylene group having 1 to 6 carbon atoms, an arylene group having 6 to 20 carbon atoms, sulfonyl group and their combinations.

The preferable examples of the above-described "–X" group will be indicated below. Moreover, examples of a group which can be used as "—L—SO$_2$—X" will be indicated as described later.

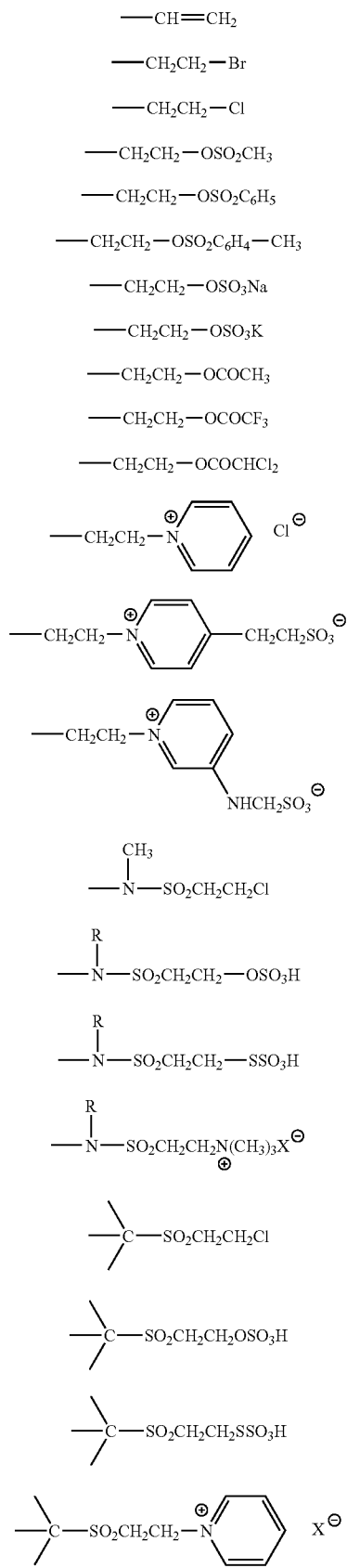

(X1) —CH=CH₂
(X2) —CH₂CH₂—Br
(X3) —CH₂CH₂—Cl
(X4) —CH₂CH₂—OSO₂CH₃
(X5) —CH₂CH₂—OSO₂C₆H₅
(X6) —CH₂CH₂—OSO₂C₆H₄—CH₃
(X7) —CH₂CH₂—OSO₃Na
(X8) —CH₂CH₂—OSO₃K
(X9) —CH₂CH₂—OCOCH₃
(X10) —CH₂CH₂—OCOCF₃
(X11) —CH₂CH₂—OCOCHCl₂

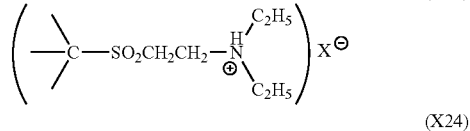
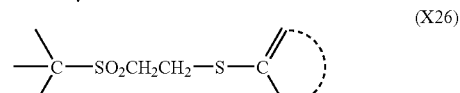
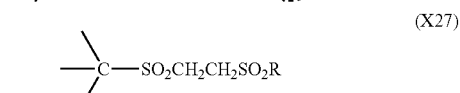
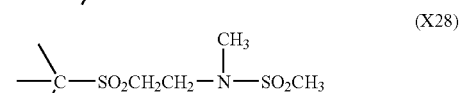
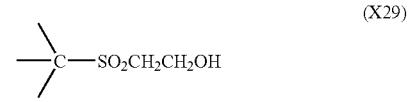

In the above-described examples, it is preferable that "—X" represents (X1), (X2), (X3), (X4), (X7), (X8), (X13) or (X14) It is more preferable that "—X" represents (X1) or (X2). It is particularly preferable that "—X" represents a vinyl group represented by (X1).

Preferable examples of L will be indicated below. "a" represents an integer of 1 to 6, preferably 1 or 2, and particularly preferably 1. "b" represents an integer of 0 to 6, and preferably either 2 or 3.

(L1) —(CH₂)ₐ—
(L2) —(CH₂)ₐ—O—(CH₂)ₐ—
(L3) —(CH₂)ₐ—CONR¹¹—(CH₂)ᵦ—NR¹¹CO—(CH₂)ₐ—
(L4) —(CH₂)ₐ—SO₂—(CH₂)ₐ—

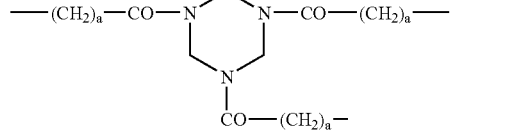

As for L, in addition to the above-described bivalent linking groups, a group that a hydrogen atom of the alkylene group in the above-described formula is substituted with a —SO$_2$CH=CH$_2$ group is also preferable.

As for a bifunctional reactive compound utilized for obtaining a solid support to which a vinyl sulfonyl group represented by the foregoing formula (1) or its reactive precursor group is fixed by covalent bond, a disulfone compound represented by the following formula (2) can be advantageously utilized.

$$X^1\text{—SO}_2\text{—L}^2\text{—SO}_2\text{—X}^2 \quad (2)$$

[In the above-described formula, each of $X^1$ and $X^2$ independently from each other represents —CR$^1$=CR$^2$R$^3$ or —CHR$^1$—CR$^2$R$^3$Y (reactive precursor group); each of R$^1$, R$^2$ and R$^3$ independently from each other represent an atom or a group selected from the group consisted of a hydrogen atom, an alkyl group having 1 to 6 carbon atoms, an aryl group having 6 to 20 carbon atoms, and an aralkyl group having 7 to 26 carbon atoms in total containing an alkyl chain having 1 to 6 carbon atoms; Y represents an atom or a group selected from the group consisted of a halogen atom, —OSO$_2$R$^{11}$, —OCOR$^{12}$, —OSO$_3$M and quaternary pyridinium group; R$^{11}$ represents a group selected from the group consisted of an alkyl group having 1 to 6 carbon atoms, an aryl group having 6 to 20 carbon atoms and an aralkyl group having 7 to 26 carbon atoms in total containing an alkyl chain having 1 to 6 carbon atoms; R$^{12}$ represents a group selected from the group consisted of an alkyl group having 1 to 6 carbon atoms and a halogenated alkyl group having 1 to 6 carbon atoms; M represents an atom or a group selected from the group consisted of a hydrogen atom, an alkali metallic atom and ammonium group; and L$^2$ represents a linking group].

Specifically, a reactive solid support used in the present invention can be easily manufactured by bringing a disulfone compound represented by the above-described formula (2) into contact with the above mentioned solid support, for example in the aqueous atmosphere.

The representative examples of disulfone compound preferably used in the present invention will be shown in the followings. It should be noted that a disulfone compound might be used by mixing two types or more.

(S1)

(S2)

(S3)

(S4)

(S5)

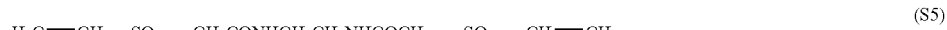
(S6)

(S7)

(S8)

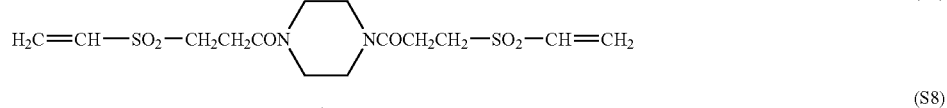
(S9)

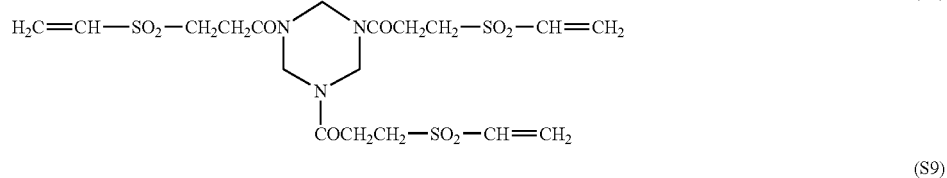
(S10)

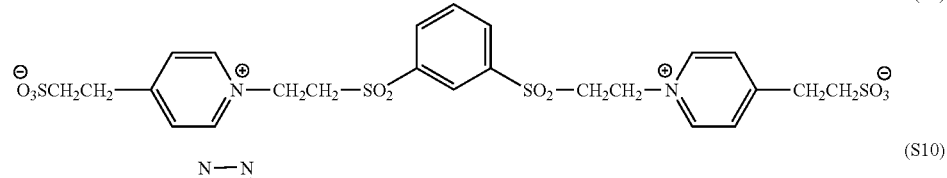
(S11)

(S12)

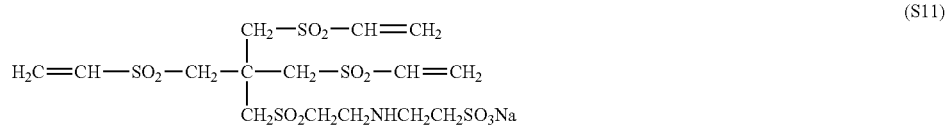

-continued

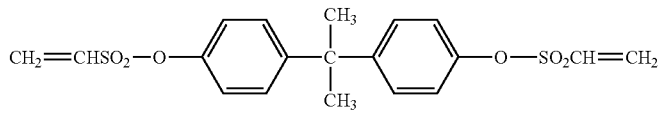
(S13)

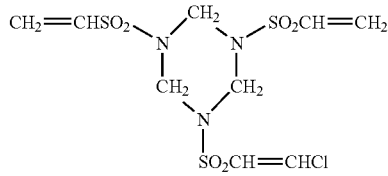
(S14)

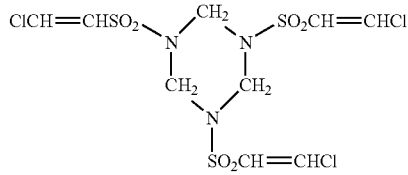
(S15)

Representative examples of disulfone compound represented by the above-described formula (2) include 1,2-bis (vinylsulfonylacetamide)ethane [corresponding to the above-described S1].

As for a method for synthesizing a disulfone compound used in the present invention, the details have been described in a variety of gazettes, for example, such as Japanese Patent Publication No. S47-2429, Japanese Patent Publication No.S50-35807, Japanese Unexamined Patent Publication No.S49-24435, Japanese Unexamined Patent Publication No. S53-41551, Japanese Unexamined Patent Publication No. S59-18944 or the like.

In order to prepare a detection tool (in general, referred to as a DNA chip) for detecting by fixing a polynucleotide or an oligonucleotide originally from the nature such as DNA, RNA, DNA fragments, RNA fragments or the like by utilizing the reactive solid support obtained as described above, a method for bringing the above-described reactive solid support into contact with a nucleotide derivative or its analog equipped with a reactive group such as amino group which reacts with a vinyl sulfonyl group or its reactive precursor group on the above-described support surface to form a covalent bond is utilized. That is to say, in this way, a detection tool equipped with a probe molecule of the desired nucleotide derivative or its analog (a nucleic acid-fixed solid support, such as what is called a DNA chip) can be prepared.

The binding of a vinyl sulfonyl group or its reactive precursor group to the surface of a solid phase support via covalent bond has a strong resistance to heat, and also the binding of a nucleic acid to the group of vinylsulfonyl group or its reactive precursor has a strong resistance to heat. Therefore, in the present invention, a PCR reaction (which contains heat treatment) can be performed by adding a template nucleic acid to a solid support on which a nucleic acid is fixed. The use of such a heat resistant solid support on which a nucleic acid is fixed is one of the advantages of the present invention. A vinyl sulfonyl group or its reactive precursor group bound via covalent bond to the surface of a solid phase support can be readily preserved in a stable state since it has a high resistance to the hydrolysis, and can form a stable covalent bond by rapidly reacting with a nucleotide derivative or a reactive group of its analog in which amino group has been previously provided or a reactive group such as amino group has been introduced.

Representative examples of a nucleotide derivative and its analog used as a probe molecule include an oligonucleotide, a polynucleotide, and a peptide nucleic acid. These nucleotide derivatives or their analogs may be originally from the nature (DNA, DNA fragment, RNA or RNA fragment), or may be a synthetic compound. Moreover, nucleotide derivatives or its analog include a variety of analogous compounds such as what is called a LNA having a crosslinking group at its sugar unit portion (J. Am. Chem. Soc. 1998, 120: 13252–13253) are included.

In the case where DNA fragments are used as a probe molecule, these are divided into two types depending on purposes. In order to examine the expression of a gene, it is preferable to use a polynucleotide such as cDNA, one portion of cDNA, or EST. Functions of these polynucleotides may be unknown, but in general, these are prepared by amplifying cDNA library, genomic library, or the total genome as a template on the basis of the sequences registered on a data base by a PCR method (hereinafter, referred to as "PCR product"). Ones not amplified by a PCR method can be also preferably used. In order to examine the mutation and polymorphism of a gene, it is preferable to synthesize a variety of oligonucleotides corresponding to mutation and polymorphism based on the known sequence which is to be the standard, and use them. Furthermore, in the case where the purpose is to analyze the base sequence, it is preferable to synthesize $4^n$ (n represents the length of the base) species of oligonucleotides and use them. As for the base sequence of a DNA fragment, it is preferable that its sequence has been previously determined by a general base sequence determination method. The size of the DNA fragment is preferably from dimmer to 50-mer, and particularly preferably from 10- to 25-mer.

On one end of a nucleotide derivative such as an oligonucleotide and a DNA fragment, or its analog, a reactive group which forms a covalent bond by reacting with the foregoing vinyl sulfonyl group or its reactive precursor group is introduced. Such reactive groups include an amino group, an imino group, hydrazino group, carbomoyl group, hydrazinocarbonyl group or carboxyimido group, and the amino group is particularly preferable. The reactive group is usually bound to an oligonucleotide or a DNA fragment via a crosslinker. As the crosslinker, for example, an alkylene group or a N-alkylamino-alkylene group is utilized, and a hexylene group or a N-methylamino-hexylene group is preferable, and a hexylene group is particularly preferable. It should be noted that since a peptide nucleic acid (PNA) has an amino group, usually it is not necessary to introduce another reactive group.

Bringing a nucleotide derivative or its analog having a reactive group into contact with a reactive solid support is usually carried out by dotting the aqueous solution of the nucleotide derivative or its analog to the surface of the reactive solid support. Concretely, it is preferable that after an aqueous solution is prepared by dissolving or dispersing the nucleotide derivative or its analog having a reactive group in an aqueous medium, the aqueous solution is pipetted into 96 wells or 384 wells plastic plate, and the pipetted aqueous solution is dropped on the surface of the solid support using a spotter device or the like.

In order to prevent the nucleotide derivative or its analog from being dried after the dotting, a substance having a high boiling point may be added in the aqueous solution in which the nucleotide derivative or its analog is dissolved or dispersed. The substance having a high boiling point is preferably a substance that can be dissolved in the aqueous solution in which the nucleotide derivative or its analog to be dotted is dissolved or dispersed, does not hinder hybridization with a sample such as a nucleic acid fragment sample (target nucleic acid fragment) which is an object of the detection, and has a not very high viscosity. Such substances include glycerin, ethylene glycol, dimethyl sulfoxide and a hydrophilic polymer having a lower molecular weight. Examples of the hydrophilic polymers include polyacrylamide, polyethylene glycol and sodium polyacrylate. Preferable molecular weight of this polymer is in the range from $10^3$ to $10^6$. As the substance having a high boiling point, it is more preferable to use glycerin or ethylene glycol, and particularly preferable to use glycerin. Preferable concentration of the substance having a high boiling point is in the range from 0.1 to 2% by volume, and particularly preferably 0.5 to 1% by volume in the aqueous solution of the nucleotide derivative or its analog.

Moreover, for the sake of the same purpose, it is also preferable to place the solid support after the dotting of a nucleotide derivative or its analog under the circumstances where the humidity is 90% or more and the temperature is in the range from 25 to 50° C.

A post-treatment by ultraviolet ray, sodium borohydride or Schiff reagent may be carried out after the dotting of the nucleotide derivative or its analog having a reactive group. These post-treatments may be carried out by combining a plurality kinds of them, and the combination of heating treatment and the ultraviolet ray treatment is particularly preferable. These post-treatments are particularly effective in the case where the surface of the solid support is treated only by a polycationic compound. Incubation after the dotting is also preferable. After the incubation, removal of unreacted nucleotide derivatives or its analogs by washing is preferable.

A preferable fixed amount (numerical quantity) of nucleotide derivatives or its analogs with respect to the surface of the solid support is in the range from $10^2$ to $10^5$ per $cm^2$. A preferable amount of nucleotide derivatives or its analogs is in the range from 1 to $10^{-15}$ mol, and is several ng or less in weight. By dotting, the aqueous solution of nucleotide derivatives or its analogs is fixed in a dot shape to the surface of the solid support. The shape of the dot is nearly circular.

No variation in the shape is important for the quantitative analysis of a gene expression and the analysis of single nucleotide polymorphism. A preferable distance between each dot is in the range from 0 to 1.5 mm, and a particularly preferable distance is in the range from 100 to 300 μm. As for the size of a dot, a preferable diameter of it is in the range from 50 to 300 μm. A preferable amount of the solution containing nucleotide derivatives or its analogs for dotting to the surface of the solid support is in the range from 100 pL to 1 μL, and a particularly preferable amount is in the range from 1 to 100 nL.

FIG. 1 schematically shows a method for manufacturing an oligonucleotide fixed solid support and a configuration of a representative oligonucleotide fixed solid support.

As a method for manufacturing a solid support to which an oligonucleotide is fixed, in the case where a disulfone compound represented by the foregoing formula (2) is employed, four types of methods for manufacturing can be utilized depending on $X^1$ and $x^2$.

FIG. 1 shows (a) a method for manufacturing a solid support (C1) to which the oligonucleotide is fixed using a disulfone compound of the formula (2) of which both of $X^1$ and $X^2$ represent —$CHR^1$—$CR^2R^3Y$ (reactive precursor group), and (b) a method for manufacturing an oligonucleotide fixed solid support (C2) using the disulfone wherein $X^1$ represents —$CHR^1$—$CR^2R^3Y$ and $X^2$ represents —$CR^1$=$CR^2R^3$. Here, supposing that $X^1$ represents a group reacting in the first place with a reactive group (R) introduced on the surface of the solid support 1, a method for manufacturing the solid support using the disulfone where $X^1$ represent —$CR^1$=$CR^2R^3$ may also be useful. Hereinafter, description will be made supposing that "$X^1$" is a group reacting in the first place with a reactive group (R) introduced on the surface of the solid support 1.

The manufacturing methods (a) and (b) will be described below.

Step (1): A —$(CR^1R^2)_n$—$SO_2$—L—$SO_2$—$X^2$ group is introduced to the solid support by bringing a disulfone compound represented by the formula (1) into contact with the surface of the solid support 1 into which the reactive group (R) is introduced [solid support (A)], and substituting —Y portion of X1 with a reactive group (R).

Step (2): A reactive group (Z) is added by bringing an oligonucleotide 2 having a reactive group (Z) at one end into contact with $X^2$ of —$(CR^1R^2)_n$—$SO_2$—L—$SO_2$—$X^2$ group introduced in the Step (1), or —Y of the $X^2$ is substituted with the reactive group (Z) by bringing the oligonucleotide 2 into contact with Y.

A support of the present invention for fixing a probe molecule may be manufactured by the following method using —$CR^1$=$CR^2R^3$ as $X^1$, supposing that $X^1$ is a group reacting in the first place with the reactive group (R) introduced to the surface of the solid support 1.

Step (1): A —$R^3R^2C$—$R^1HC$—$SO_2$—L—$SO_2$—$X^2$ group is introduced to the surface of the solid support by bringing a disulfone compound represented by the formula (I) into contact with the surface of the solid support (A) consisted of solid support having the convex and concave portions (solid support 1) to the surface of which the active group (R) is introduced, and adding the reactive group (R) to —$CR^1$=$CR^2R^3$ of $X^1$.

Step (2): The reactive group (Z) is added by bringing an oligonucleotide having the reactive group (Z) at one end into contact with X2 of —$R^3R^2C$—$R_1HC$—$SO_2$—L—$SO_2$—$X_2$ group introduced in the Step (1), or —Y of the $X_2$ is substituted with the reactive group (Z) by bringing the oligonucleotide 2 into contact with Y.

The oligonucleotide having the reactive group (Z) at one end is a compound shown by the reference numeral 2 in FIG. 1. A crosslinker (Q), though it is not essential, exists in general between the reactive group (Z) and phosphate ester group as a matter of convenience for preparation. A -phosphate group-NNNN , , , NN represents an oligonucleotide. $R^4$ represents a group determined by the reaction between the reactive group (R) and $X^1$, and $Z^1$ represents a group determined by the reaction between $X^2$ and the reactive group (Z), respectively.

When the oligonucleotide 2 having the reactive group (Z) is dotted to the surface of the solid support (B) having the convex and concave portions shown in FIG. 1, although the reaction between $X^2$ or —Y of $X^2$ and the reactive oligonucleotide fragment 2 is occurred, an unreacted $X^2$ to which the oligonucleotide 2 is not bound also exists on the surface of solid support (B). In this case, there is a possibility that such $X^2$ reacts in a non-specific manner with a labeled nucleic acid fragment sample in a hybridization to be performed later resulting in a problem that non-specific binding may be measured. Therefore, it is preferable that the $X^2$ (i.e., a halogen atom of $X^2$, for example) has been previously subjected to a masking treatment. It is preferable that the masking treatment is performed by bringing an anionic compound having an amino group or a mercapto group into contact with the surface of the solid support (C) (or (C2)). Since the oligonucleotide 2 has a negative charge, the oligonucleotide 2 can be prevented from reacting with the unreacted $X^2$ by generating negative charge also on the surface of the solid support (C). As for such an anionic compound, any one can be used if it reacts with a halogen atom of $X^2$ and has a negative charge ($COO^-$, $SO_3^-$, $OSO_3^-$, $PO_3^-$, or $PO_2^-$). Among them, an amino acid is preferable, and glycine or cysteine is particularly preferable. Further, taurine is also preferably used.

The shelf life of a solid support manufactured according to the present invention, in which a nucleotide derivative or its analog is fixed, is usually several weeks for a cDNA fixed solid support to which cDNA is fixed, and the shelf life of a solid support to which a synthesized oligonucleotide is fixed is further longer. A solid support of the present invention to which an oligonucleotide or its analog is fixed is utilized for monitoring the gene expressions, determining the base sequences, analyzing the mutations, analyzing the polymorphism or the like. The principle of the detection is based on the hybridization with the labeled sample nucleic acid fragment, which will be described later.

In the present invention, a labeled sample nucleic acid fragment is prepared by adding a template nucleic acid to the solid support to which a nucleic acid has been fixed, and performing a PCR reaction or a reverse transcription reaction.

As for the sample nucleic acid, a nucleic acid sample such as a DNA sample or an RNA sample whose sequence or function is unknown is usually used. A labeled sample nucleic acid fragment is prepared by adding the sample nucleic acid as a template onto the solid support, and performing a PCR reaction or a reverse transcript reaction.

As a labeling method, an RI method and a non-RI method (fluorescence method, biotin method, chemiluminescence method or the like) are known, and in the present invention, use of the fluorescence method is preferable. As for a fluorescent substance utilized for a fluorescent labeling, although any can be used if it can bind to the basic portion of nucleic acid. For example, a cyanine dye (e.g., Cy3, Cy5 or the like of Cy Dye™ series, which is commercially available), rhodamine 6G reagent, N-acetoxy-N-2-acetylaminofluorene (AAF) or AAIF (iodine derivative of AAF) can be used.

A nucleic acid labeled with a labeling substance can be synthesized by adding the labeling substance(s) into a reaction mixture for the PCR reaction or the reverse transcription reaction and performing a synthesizing reaction of a nucleic acid.

It is preferable that a nucleic acid fragment sample is isolated from the cell or tissue sample of eucaryote for the purpose of examining the gene expression. In the case where the sample is a genome, it is preferably isolated from any given tissue sample except for red blood cell. It is preferable that any given tissue except for red blood cell is peripheral blood lymphocyte, skin, hair, sperm or the like. In the case where the sample is an mRNA, it is preferable that it is extracted from the tissue sample in which the mRNA is expressed. It is preferable that a labeled cDNA is prepared from mRNA by incorporating a labeled dNTP ("dNTP" means a deoxyribonucleotide in which the base is adenine (A), cytosine (C), guanine (G) or thymine (T)) using reverse transcription reaction. As a dNTP, use of dCTP is preferable because of chemical stability.

Although the amount of the mRNA required for one hybridization is different depending on the amount of liquid to be spotted, and the type of labeling material, it is several μg or less. It is desired that the nucleic acid fragment sample has been previously depolymerized in the case where a DNA fragment on the nucleotide derivative or its analog fixed solid support is an oligoDNA. In the case of a prokaryotic cell, since the selective extraction of an RNA is difficult, it is preferable that the total RNA is labeled.

For the purpose of detecting mutation or polymorphism of a gene, the labeled nucleic acid is preferably obtained by performing PCR of a target region in a reaction system containing a labeled primer or a labeled dNTP.

According to the present invention, hybridization can be performed by leaving the solid support as it is at a temperature suited to the hybridization, after adding a template nucleic acid to the solid support to which a nucleic acid is fixed and carrying out a PCR reaction or a reverse transcription reaction. In conventional methods, hybridization was carried out by dotting an aqueous fluid in which labeled nucleic acid fragment samples were dissolved or dispersed, which had been previously pipetted into a 96 wells or a 384 wells plastic plate, to the solid support to which nucleotide derivatives or its analogs were fixed. However, such dotting operation is not required in the method of the present invention.

The temperature and period of time of hybridization may be appropriately set. In general, hybridization is preferably carried out in the temperature range of room temperature to 70° C. in the period of 6 to 20 hours.

After the termination of the hybridization, it is preferable that washing are performed using a mixed solution of a surfactant and a buffer solution to remove unreacted nucleic acid fragment samples. As a surfactant, it is preferable to use sodium dodecyl sulfate (SDS). As a buffer solution, citrate buffer solution, phosphate buffer solution, borate buffer solution, Tris buffer solution, Good' buffer solution or the like can be used. It is particularly preferable to use citrate buffer solution.

The hybridization using the solid support to which nucleotide derivatives or its analogs are fixed is characterized in that the amount of usage of the labeled nucleic acid fragment samples can be decreased to a very minute amount. Therefore, it is necessary to set the optimal conditions of the hybridization depending on the length of chain of the nucleotide derivatives or its analogs fixed to the solid support and the types of the labeled nucleic acid fragment samples. For the analysis of gene expression, it is preferable that a hybridization for a long time period is performed so as to be capable of sufficiently detecting even a lower expressing gene. For the detection of a single nucleotide polymorphism, it is preferable that a hybridization for a short period is performed. Moreover, it is also characterized in that comparison or quantitative determination of the expression amount are made possible using a single solid support to which DNA fragments are fixed by previously preparing two types of the nucleic acid fragment sample labeled by fluorescent substances different from each other and using them in a hybridization at the same time.

The present invention will be more concretely described below by the following examples, but the present invention is not limited by these examples.

EXAMPLE

Example 1

Simultaneous Progress of PCR Reaction and Hybridization Reaction on Oligo-microarray (1) Preparation of a DNA Fragment:

A DNA fragment (22 mer, GATCAGACAC TTCAAG-GTCT AG; SEQ ID No.1) having a specific sequence originated in human liver was designed as an oligonucleotide for fixation (I). At the same time, an oligonucleotide (21 mer, ATTACAGGGT CAACTGCTAT G; SEQ ID No.2) which is irrelevant to the above-mentioned DNA fragment, was also designed as a negative control (II).

(2) Preparation of Solid Support to Which Vinylsulfonyl Group is Introduced

After immersing a slide glass (24 mm×72 mm) in an ethanol solution of aminopropylethoxy silane (2% by weight) (Shin-Etsu Chemical) for 10 minutes, the slide glass was taken out of the solution. Then, the slide glass was washed with ethanol, dried at 110° C. for 10 minutes to prepare a silane compound-coated slide glass (A). Next, the silane compound-coated slide glass was immersed in a phosphate buffer (pH 8.5) of 1,2-bis (vinylsulfonylacetamide) ethane (5% by weight) for 1 hour. Then, the slide glass was taken out of the solution, washed with acetonitrile, dried for 1 hour under a reduced pressure. Thus, a solid support (B) to the surface of which the vinylsulfonyl group was introduced was obtained.

(3) Fixation of DNAs

An aqueous solution prepared by dispersing the above-described DNA fragment for fixation in sterilized water ($1\times10^{-6}$ M) was dotted to the solid support (B) obtained in the above-described step (2) (slide glass to which vinylsulfonyl group is introduced) by using a spotting device.

The solid support after the dotting was left all night in a chamber conditioned with the saturated saline solution to sufficiently progress the binding reaction between the solid support and the DNA. Then, blocking treatment was carried out in a dyeing bat containing a blocking solution (0.1M glycin, 0.1M NaCl (pH=8.5), 0.2% SDS and 2% dextran sulfate) by shaking up und down the solid support at room temperature for 30 minutes.

After the blocking treatment, the solid support was washed in Milli-Q water at room temperature for 3 minutes (the washing was repeated twice). Then, the solid support was immersed in chilled ethanol for 3 minutes, and was dried at room temperature.

(4) PCR Reaction and Hybridization

A solution of the following composition was prepared for a PCR reaction, and was dotted to the above-mentioned slide glass. After protection of the surface of the slide glass with a cover glass for microscopy, the solid support was placed in Thermal Cycler (Thermodynamic Co.,) for In situ that had been previously regulated.

Thereafter, a PCR reaction and hybridization were simultaneously carried out by adjusting the temperature according to the following program.

| Composition of the PCR solution: | |
|---|---|
| 10 X Buffer (Gene Taq FP attached) | 4 µL |
| dNTP Mixture | 4 µL |
| (2.5 mM dATP; 2.5 mM dGTP; 2.5 mM dATP; 1.5 mM dTTP) | |
| 1 mM Cy5-dUTP | 4 µL |
| 5 µM Primer (U) | 0.5 µL |
| 5 µL Primer (L) | 0.5 µL |
| Template DNA (cDNA from human liver) | 10 ng |
| Gene Taq FP (Nippon Gene Co.) | 5 units |
| Sterilized water | adjusted to total quantity of 40 µL |
| Primer (U) : ACCCCCGGAA AACACGCACA GT | (SEQ ID NO:3) |
| Primer (L) : TCAGGCACTT TCATTAACAG GCACA | (SEQ ID NO:4) |
| Temperature conditions: | |
| 5 minutes at 95° C.; | |
| 25 cycles of 30 seconds at 95° C., 30 seconds at 55° C. and 90 seconds at 72° C. (PCR); | |
| 3 minutes at 72° C. and 2 hours at 60° C. (hybridization) | |

(5) Washing and Detection

After completion of the above-mentioned reaction, the slide glass was taken out, and the cover glass was carefully removed in a mixed solution of 0.1% by weight SDS and 2×SSC. Then, the slide glass was sequentially washed in the mixed solution for 5 minutes at room temperature, and in a mixed solution of 0.1% by weight SDS and 0.2×SSC for 5 minutes at 50° C., and in a aqueous solution of 0.2×SSC for 1 minute at room temperature. Next, the slide glass was centrifuged at 600 rpm for 20 seconds and dried at room temperature. Fluorescence intensity of the dried slide glass was measured with a florescence scanner (FLA-8000; FUJI PHOTO FILM Co.,) The results were 5500 for an oligonucleotide (I) (which has a complementary sequence to the analyte) and 720 for an oligonucleotide (II) (negative control).

From the above-described results, it is understood that the analyte hybridizes only to the oligonucleotide that was complementary to the analyte. Thus, the sample has been amplified by the PCR reaction and the amplified DNA can correctly hybridize to a specific sequence by hybridization.

INDUSTRIAL APPLICABILITY

The present invention provides a means for analyzing a gene simply and easily without performing complicated operations.

The invention claimed is:

1. A method for the detection of a nucleic acid, comprising the steps of:
performing a PCR reaction or a reverse transcription reaction on a template nucleic acid in the presence of a solid support on which a nucleic acid is fixed; and then
hybridizing the nucleic acid fixed on said solid support with the nucleic acid synthesized by the PCR reaction or the reverse transcription reaction, wherein the hybridizing step is carried out after the PCR reaction or the reverse transcription reaction by selecting a suitable hybridization temperature and without moving the solid support;
wherein a nucleotide to which a detectable label is introduced is synthesized in the PCR reaction or the reverse transcription reaction.

2. The method for the detection according to claim 1, wherein the nucleic acid is fixed on the surface of the solid support to which a group of vinylsulfonyl group or its reactive precursor has been fixed respectively by covalent bond via a linking group.

3. The method for the detection according to claim 2, wherein a linked body of the vinylsulfonyl group or its reactive precursor and the linking group is shown by the following formula:

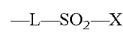

in the formula, X represents —CR$^1$=CR$^2$(R$^3$) or —CH(R$^1$)—CR$^2$(R$^3$)(Y); each of R$^1$, R$^2$ and R$^3$ represents independently from each other an atom or a group selected from the group consisting of a hydrogen atom, an alkyl group having 1 to 6 carbon atoms, an aryl group having 6 to 20 carbon atoms and an aralkyl group having 7 to 26 carbon atoms in total containing an alkyl chain having 1 to 6 carbon atoms; Y represents an atom or a group selected from the group consisting of a halogen atom, —OSO$_2$R$^{11}$, —OCOR$^{12}$, —OSO$_3$M and a quaternary pyridinium group; R$^{11}$ represents a group selected from the group consisting of an alkyl group having 1 to 6 carbon atoms, an aryl group having 6 to 20 carbon atoms and an aralkyl group having 7 to 26 carbon atoms in total containing an alkyl chain having 1 to 6 carbon atoms; R$^{12}$ represents a group selected from the group consisting of an alkyl group having 1 to 6 carbon atoms and a halogenated alkyl group having 1 to 6 carbon atoms; M represents an atom or a group selected from the group consisting of a hydrogen atom, an alkali metal atom and an ammonium group; and L represents a linking group.

4. The method for the detection according to claim 3, wherein X is a vinyl group represented by —CH=CH$_2$.

5. The method for the detection according to claim 3, wherein L is a linking group containing an atom of bivalent or more other than a carbon atom.

6. The method for the detection according to claim 3, wherein L is a linking group having a linking portion selected from the group consisting of —NH—, —S— and —O—.

7. The method for the detection according to claim 3, wherein L is a linking group represented by —(L$^1$)$_n$—NH—(CR$^1$R$^2$)$_2$— or —(L$^1$)$_n$—S—(CR$^1$R$^2$)$_2$—; L$^1$ represents a linking group; and n is 0 or 1.

8. The method for the detection according to claim 3, wherein L is a linking group represented by —(L$^1$)$_n$—NHCH$_2$CH$_2$— wherein L$^1$ represents a linking group; and n is 0 or 1.

9. The method for the detection according to claim 7 or 8, wherein L$^1$ is a linking group containing a group represented by —OSi— and n is 1.

10. The method for the detection according to claim 1, wherein the solid support is a sheet-like substrate selected from the group consisting of a glass substrate, a resin substrate, a glass substrate or a resin substrate the surface of which is treated with a silane coupling agent, and a glass substrate or a resin substrate having a covering layer on its surface.

11. The method for the detection according to claim 10, wherein the solid support is a sheet-like substrate selected from the group consisting of a silicate glass substrate, a silicate glass substrate the surface of which is treated with a silane coupling agent, and a silicate glass substrate the surface of which is covered with an organic covering layer.

12. The method for the detection according to claim 1, wherein the nucleic acid fixed on the solid support is a nucleotide derivative or its analog.

13. The method for the detection according to claim 12, wherein the nucleotide derivative or its analog is an oligonucleotide, a polynucleotide or a peptide nucleic acid.

14. The method for the detection according to claim 1, wherein said PCR reaction conditions comprise 25 cycles of 30 seconds at 95° C., 30 seconds at 55° C. and 90 seconds at 72° C.

15. The method for the detection according to claim 1, wherein said hybridization occurs after 3 minutes at 72° C. and 2 hours at 60° C.

* * * * *

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 1
gatcagacac ttcaaggtct ag                                           22

<210> SEQ ID NO 2
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 2
attacagggt caactgctat g                                            21

<210> SEQ ID NO 3
<211> LENGTH: 22
<212> TYPE: DNA
<213> ORGANISM: Artificial Sequence
<220> FEATURE:
<223> OTHER INFORMATION: Synthetic PCR primer

<400> SEQUENCE: 3
acccccggaa aacacgcaca gt                                           22

<210> SEQ ID NO 4
<211> LENGTH: 25
<212> TYPE: DNA
<213> ORGANISM: Artificial Sequence
<220> FEATURE:
<223> OTHER INFORMATION: Synthetic PCR primer

<400> SEQUENCE: 4
tcaggcactt tcattaacag gcaca                                        25
```